US00PP09175P

United States Patent [19]

Dehan

[11] Patent Number: Plant 9,175

[45] Date of Patent: Jun. 20, 1995

[54] ASTER PLANT NAMED 'SUNSOL'

[75] Inventor: Klara Dehan, Holon, Israel

[73] Assignee: Danziger—"Dan" Flower Farm, Post Beit Dagan, Israel

[21] Appl. No.: 291,699

[22] Filed: Aug. 16, 1994

[51] Int. Cl.[6] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A new and distinct cultivar of aster plant named Sunsol, characterized by its white ray floret color; deep yellow tubular discs; strong and rigid stems, each of which carries many flowers; excellent branching, and early flowering.

1 Drawing Sheet

The present invention comprises a new and distinct cultivar of Aster plant, botanically known as *Aster ericoides,* hereinafter referred to by the cultivar name Sunsol.

The new cultivar was originated from a cross made in a controlled breeding program by the inventor Klara Dehan in Mishmar Hashiva, Israel.l Both the female, or seed, and the male, or pollen parents were cultivars of *Aster ericoides* which are unknown at this time. Both parents are proprietary lines used exclusively for breeding.

Sunsol was discovered and selected by the inventor as a flowering plant within the progeny of the stated cross in a controlled environment in Mishmar Hashiva, Israel. Asexual reproduction of the new cultivar by leaf cuttings performed by the inventor at Mishmar Hashiva, Israel has demonstrated that the combination of characteristics as herein disclosed for the new cultivar are firmly fixed and retained through successive generations of asexual reproduction.

Sunsol has not been observed under all possible environmental conditions. The phenotype may vary somewhat with variations in environment such as temperature, light intensity and daylength, without, however, any variation in genotype. The following observations, measurements and values describe the new cultivar as grown in Mishmar Hashiva, Israel under conditions which closely approximate those generally used in commercial practice.

The following traits have been repeatedly observed and are determined to be basic characteristics of Sunsol which in combination distinguish this aster as a new and distinct cultivar:

1. Medium size, white flowers.
2. Deep yellow tubular disc florets.
3. Tall and rigid stems, each of which carries many flowers.
4. Very dark green, glossy foliage.
5. Early flowering.

The new cultivar can be compared to the aster Sunrio. Similar characteristics are flower size, ray floret color, long stems, and good branching. Sunsol is distinguished from Sunrio by its deep yellow tubular disc florets, smaller leaves, and earlier flowering.

The accompanying color photographic drawing illustrates a portion of a typical specimen plant of the new cultivar, with partially open and completely open flowers being illustrated. The flowers are shown enlarged relative to true size. The photo does not accurately depict the true ray floret color for Sunsol. However, the color values noted below are correct.

In the following description, color references are made to The Royal Horticultural Society Colour Chart (RHS), except where general colors of ordinary significance are referred to. Color values were taken in the morning in Mishmar Hashiva, Israel.

Classification:

*Botanical.*—*Aster ericoides* Hybrid cv. Sunsol.

*Commercial.*—Daisy-like spray or garden variety.

Parentage:

*Male parent.*—Unknown seedling of *Aster ericoides.*

*Female parent.*—Unknown seedling of *Aster ericoides.*

Propagation: The new cultivar holds its distinguishing characteristics through successive propagations by leaf cuttings.

INFLORESCENCE

A. Capitulum:

*Form.*—Daisy, generally cup-shaped.

*Type.*—Semi-double, with 1.5 to 2 rows of petals.

*Diameter across face.*—2.0 cm.

B. Corolla of ray florets:

*Color (general tonality from a distance of three meters).*—White.

*Color (upper surface).*—White 155D.

*Color (lower surface).*—White 155D.

*Shape.*—Florets are generally narrow and oblong, with apex rounded; slightly concave.

C. Corolla of disc florets:

*Color (mature).*—2C.

*Color (immature).*—12A.

*Diameter of disc.*—1 cm.

D. Flowering period: When field grown in natural season, plants planted in June will flower in September. In winter greenhouse production, preferred culture includes approximately four weeks of long-day treatment after pinching until the stems elongate to approximately 10 cm, followed by short days. From the start of short days, flowering occurs in approximately 7 weeks in the fall and 9 weeks in the winter.

E. Reproduction organs:

*Androecium.*—Stamens present on both ray and disc florets and yellow to purple in color; pollen is yellow and found only in the winter season in Israel.

*Gynoecium.*—Present on disc florets; green in color.

PLANT

A. General appearance: Excellent branching and tall and strong stems result in a great abundance of medium size white flowers; medium to tall in height, the main stem reaching a height of 1.0 to 1.2 meters in a fully grown plant.

B. Foliage:

*Color.*—147A.

*Shape.*—Linear, with occasional downward reflexing at the tip.

*Size.*—Typical leaves at upper part of plant are 35 mm in length and 3 mm in width; larger leaves at bottom of plant are 120 mm in length and 9 in width.

*Margin.*—Entire.

*Arrangement.*—Alternate, with angle acute.

I claim:

1. A new and distinct cultivar of aster plant named Sunsol, as illustrated and described.

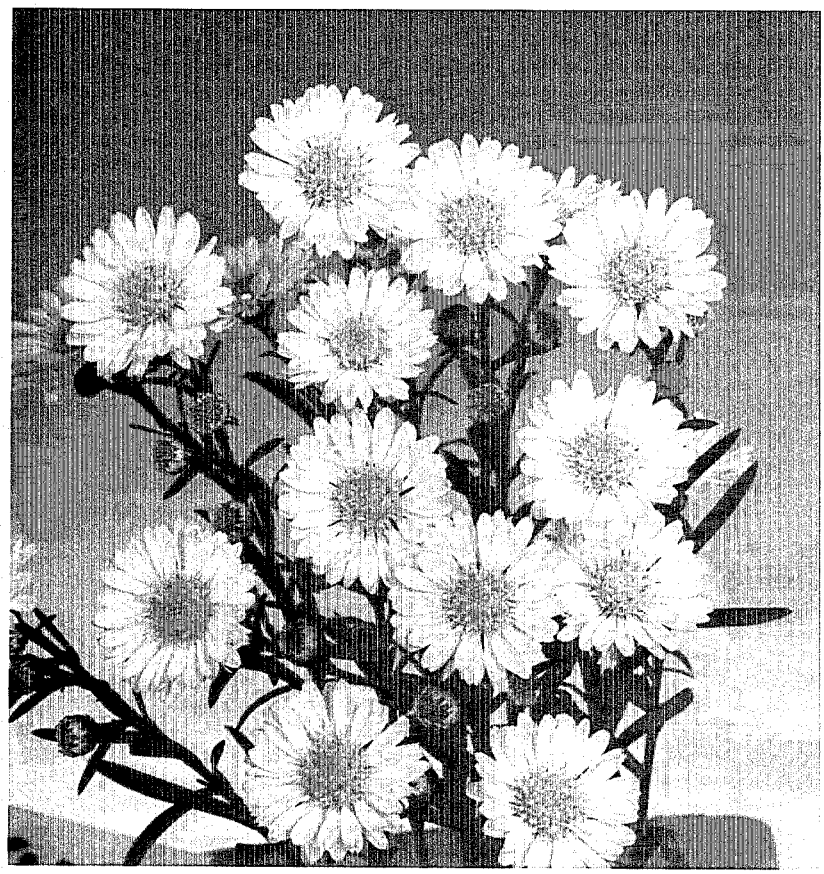

* * * * *